(12) United States Patent
Yue et al.

(10) Patent No.: US 6,335,337 B1
(45) Date of Patent: Jan. 1, 2002

(54) SUBSTITUTED PIPERAZINONES AND THEIR THERAPEUTIC USES

(75) Inventors: Christophe Yue; Marguerite Henry, both of Maisons Alfort; Thierry Giboulot, Vincennes; Brigitte Lesur, Champs-sur-Marne, all of (FR)

(73) Assignee: Laboratoire L. Lafon, Maisons Alfort (FR)

( * ) Notice: Subject to any disclaimer, the term of this patent is extended or adjusted under 35 U.S.C. 154(b) by 0 days.

(21) Appl. No.: 09/743,352

(22) PCT Filed: Jul. 16, 1999

(86) PCT No.: PCT/FR99/01751

§ 371 Date: Jan. 9, 2001

§ 102(e) Date: Jan. 9, 2001

(87) PCT Pub. No.: WO00/04001

PCT Pub. Date: Jan. 27, 2000

(30) Foreign Application Priority Data

Jul. 17, 1998 (FR) .............................................. 98 09169

(51) Int. Cl.⁷ .................... A61K 31/495; A61K 31/397; C07D 241/08; C07D 413/10

(52) U.S. Cl. .................... 514/235.8; 544/121; 544/360; 544/363; 544/367; 544/376; 544/377; 544/379; 544/393; 514/252.13; 514/253.01; 514/253.06; 514/253.07; 514/254.04; 514/254.11; 514/255.03

(58) Field of Search ................................. 544/121, 393, 544/367, 360, 363, 376, 377, 379; 514/235.8, 255.03, 253.06, 253.07, 253.01, 254.01, 254.11, 252.13

(56) References Cited

FOREIGN PATENT DOCUMENTS

| EP | 0 608 759 A3 | 8/1994 |
|---|---|---|
| EP | 0 608 759 A2 | 8/1994 |

*Primary Examiner*—Emily Bernhardt
(74) *Attorney, Agent, or Firm*—Young & Thompson

(57) ABSTRACT

Novel compounds which are inhibitors of the binding of fibrinogen to the Gp iib/iiia platelet receptors, and which can be used therapeutically as antithrombotic agents.

8 Claims, No Drawings

SUBSTITUTED PIPERAZINONES AND THEIR THERAPEUTIC USES

The present invention relates to novel compounds which are inhibitors of the binding of fibrinogen to the Gp IIb/IIIa platelet receptors, and which can be used therapeutically as antithrombotic agents.

In the course of the pathological processes which lead to the formation of a thrombus (clot) and then to its extension, platelet aggregation represents a key step since it is the source of the seriousness of the phenomenon. Specifically, from the initiation of the thrombus, in particular in the arterial blood circulation, the intervention of several interdependent biochemical reactions induces the aggregation of an increasingly large number of platelets via the conversion of the soluble fibrinogen into insoluble fibrin filaments which increase the size of the mass of platelets, first at the actual site of the arterial vascular lesion, and then increasingly into the lumen of the vessel.

In this mechanism of platelet aggregation, activation of the Gp IIb/IIIa receptors is the source of the amplification of the platelet aggregation. Fibrinogen, which can bind via its two dimers to these receptors, amplifies the binding together of the platelets and thus induces the formation of a platelet mass forming a thrombus at the site of rupture of the atheroma plaque.

This mechanism of platelet aggregation is particularly active in all arterial thromboses, whether they appear in the course of performing interventional cardiology (transluminal percutaneous angioplasty; insertion of stents), heart surgery (aorta-coronary bypass; valve surgery), in the course of acute heart diseases (myocardial infarction, unstable angina, acute coronary syndromes, etc.) or in the course of certain cerebral ischaemias, or finally in the course of myocardial ischaemias which may complicate the follow-up of an antithrombotic treatment.

Reducing or preventing the activation of platelets in contact with a broken atherosclerotic plaque thus represents a novel and effective therapeutic approach to the treatment of thrombosis, in particular arterial thrombosis, and thus an efficient means for preventing acute coronary syndromes, including unstable angina and myocardial infarction.

The present invention is directed towards novel competitive inhibitors of the binding of fibrinogen on the Gp IIb/IIIa receptors which can be used as antithrombotic medicinal products.

The present invention is also directed towards providing compounds which can be administered orally, which give a prolonged duration of action and which avoid the risks of bleeding.

One subject of the present invention is compounds of the general formula (I):

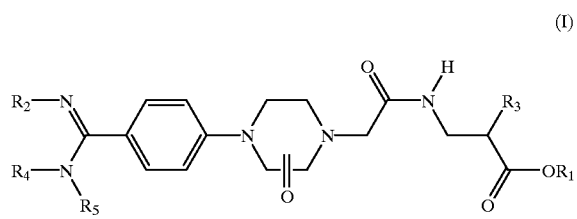

in which:
$R_1$ is chosen from hydrogen, a $C_1$–$C_4$ alkyl group and a phenyl($C_1$–$C_4$ alkyl) group;
$R_2$ is chosen from hydrogen, a hydroxyl group and a protecting group for the amidino group;

$R_3$ is chosen from the groups of formula:

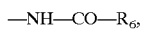

$R_6$ being chosen from $C_1$–$C_4$ alkoxy, $C_3$–$C_7$ cycloalkoxy, benzyloxy, methoxyphenyl, dimethoxyphenyl, benzodioxolyl and benzodioxanyl groups,
and the groups of formula:

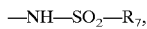

$R_7$ being chosen from:
$C_1$–$C_5$ alkyl groups optionally substituted with one or more groups chosen from halogens, hydroxyl groups and the trifluoromethyl group;
mono- or bicyclic $C_3$–$C_{12}$ cycloalkyl groups;
mono-, bi- or tricyclic $C_6$–$C_{14}$ aryl groups;
heteroaryl groups chosen from pyridyl, thienyl, quinolyl, benzodioxanyl, benzodioxolyl and isoxazolyl groups;
phenyl($C_1$–$C_4$)alkyl and naphthyl ($C_1$–$C_4$)alkyl groups;
and the groups of formula:

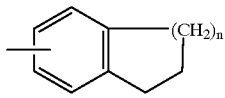

in which n=1, 2 or 3;
the aryl or heteroaryl groups of $R_7$ optionally being substituted with one or more groups chosen independently from halogens, $C_1$–$C_4$ alkyl, trifluoromethyl, $C_1$–$C_4$ alkylthio, $C_1$–$C_4$ alkyloxy, $C_1$–$C_4$ alkylsulphonyl, nitro, di (($C_1$–$C_4$)alkyl)amino, phenyl, naphthyl and heteroaryl groups chosen from thienyl, furyl and pyridyl groups, and from groups —COOR, —CH$_2$—COOR or —O—CH$_2$COOR, R being a $C_1$–$C_4$ alkyl group.
$R_4$ and $R_4$ are chosen, independently of each other, from hydrogen, a $C_1$–$C_5$ alkyl group or form, together with the nitrogen atom, a group chosen from piperidyl and morpholinyl groups,
and the oxo group is in position 2 or 3 on the piperazine, and the addition salts thereof with pharmaceutically acceptable acids.

As protecting groups for the amidino group, mention may be made of ethoxycarbonyl, benzyloxycarbonyl, p-nitrobenzyloxycarbonyl and tertbutoxycarbonyl groups.

As examples of aryl groups, mention may be made of phenyl, α-naphthyl, β-naphthyl, fluorenyl and biphenylyl groups.

The $C_1$–$C_5$ alkyl groups may be linear or branched. Examples which may be mentioned are methyl, ethyl, propyl, isopropyl, butyl, isobutyl, tert-butyl and pentyl groups.

The $C_1$–$C_4$ alkoxy groups may similarly be linear or branched. Examples which may be mentioned are methoxy, ethoxy, propoxy, isopropoxy, butoxy and isobutoxy groups.

The halogens may be chosen from fluorine, chlorine, bromine and iodine.

The "addition salts with pharmaceutically acceptable acids" denote salts which give the biological properties of the free bases without having an undesirable effect. These salts may be, in particular, those formed with mineral acids, such as hydrochloric acid, hydrobromic acid, sulfuric acid, nitric acid or phosphoric acid; acidic metal salts such as disodium orthophosphate and monopotassium sulphate, and organic acids.

The compounds of formula (I) can be prepared by:
a) reacting an acid of formula

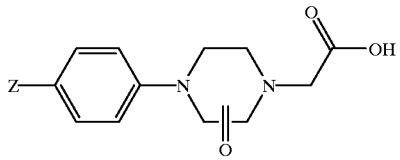

(II)

in which Z is a precursor group of a group

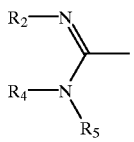

with an amine of formula

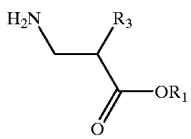

(III)

to give a compound of formula

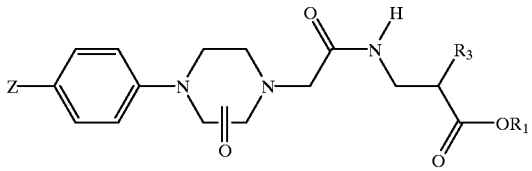

(IV)

and
b) converting the group Z into a group

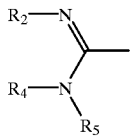

The acids of formula (II) can be reacted with the amines of formula (III) in a polar solvent such as DMF, THF or ethyl acetate, in the presence of a coupling agent (DCC/HOBT, BOP or isobutyl chloroformate) at a temperature of from 15° C. to 50° C.

When Z is an N≡C— group, the group Z can be converted into an amidoxime by adding hydroxylamine to the nitrile group in the presence of a suitable base (K$_2$CO$_3$, Et$_3$N or C$_2$H$_5$ONa) in an alcoholic solvent. Hydrogenolysis in the presence of palladium-on-charcoal, in a mixture of acetic anhydride and acetic acid, of the compounds obtained gives the compounds of formula (I) in which R$_2$ is hydrogen.

When Z is an N≡C— group, the group Z can also be converted into an imidate by adding ethanol in the presence of HCl in ethyl acetate. The imidate obtained is then converted into compounds of formula (I) in which R$_2$ is a hydrogen and —NR$_4$R$_5$ is either a piperidyl group or a morpholinyl group, by reaction with the corresponding amine in ethanol/ethyl acetate medium.

The compounds of formula (II) containing a 2-piperazinone group, when Z is a nitrile group, can be obtained according to the following scheme:

Scheme 1

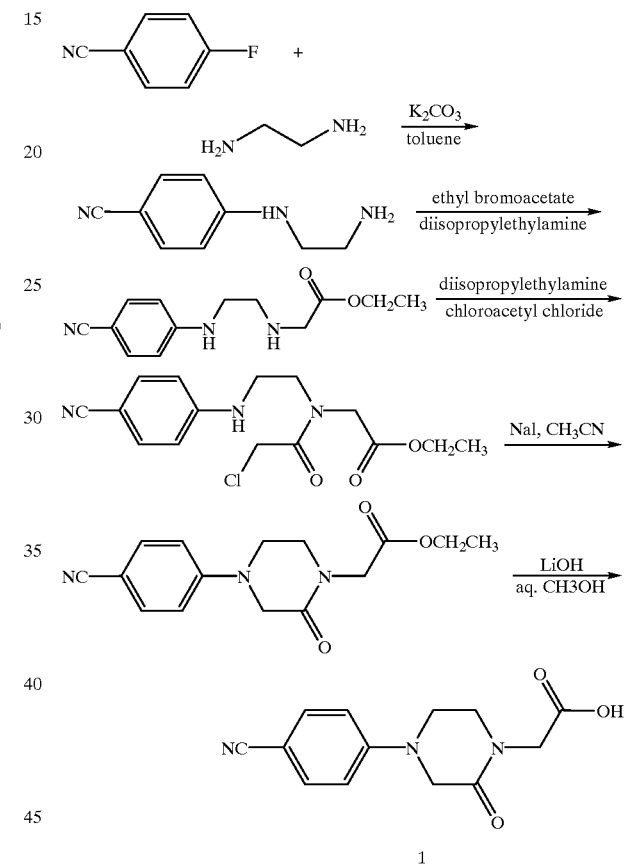

1

4-Fluorobenzonitrile is reacted with an excess of ethylenediamine in an aprotic solvent to give 4-(2-aminoethyl)benzonitrile which is then mono-alkylated with ethyl bromoacetate in a polar solvent such as ethanol or acetonitrile in the presence of an inorganic base or a tertiary amine. Acylation with chloroacetyl chloride followed by cyclization and hydrolysis give the acid (1).

The compounds of formula (II) containing a 3-piperazinone group, when Z is a nitrile group, can be obtained according to the following scheme:

Scheme 2

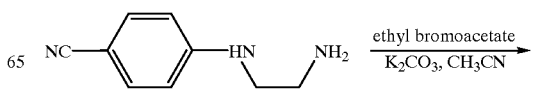

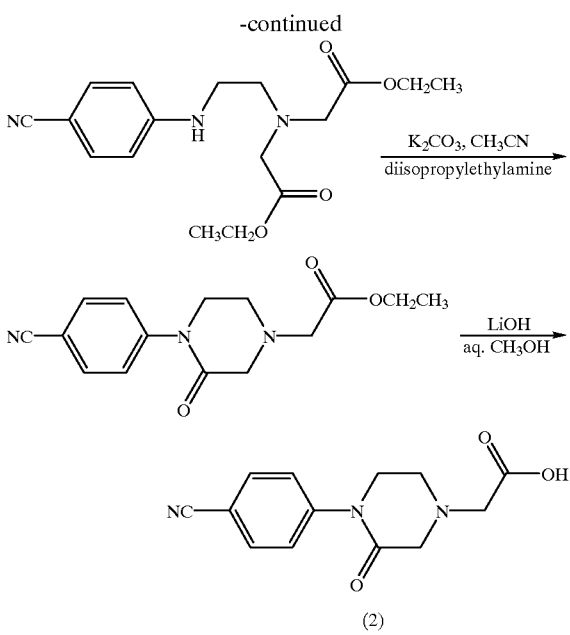

4-(2-Aminoethyl)benzonitrile is dialkylated with ethyl bromoacetate; the cyclization is carried out in the presence of a tertiary amine, an inorganic base or a mixture thereof; after hydrolysis, the acid (2) is obtained.

The addition salts are obtained conventionally by reacting the compound of formula (I) with a pharmaceutically acceptable acid in a suitable solvent. conversely, the bases may be obtained from the addition salts by treatment with a strong base.

The examples which follow illustrate the preparation of the compounds of formula I.

A—Preparation of the Compounds of Formula II

A-1: Synthesis of 2-[4-(4-cyanophenyl)-2-oxopiperazino] acetic acid (compound 1)

a) 4-(2-Aminoethylamino)benzonitrile (compound 1a)

A suspension of 4-fluorobenzonitrile (167 g, 1.38 mol), ethylenediamine (330 g, 5.5 mol) and potassium carbonate (300 g, 2.17 mol) in 2 l of toluene is refluxed for 6 hours. After cooling to room temperature, the mixture is filtered and rinsed with toluene, and the filtrate is evaporated to give a yellow oil which is crystallized from toluene. The product is filtered off, rinsed with toluene and dried under vacuum at 50° C. to give 200 g of a slightly yellow solid.

Yield=90%; Melting point=85° C.; $^1$H-NMR (400 MHz, CDCl$_3$): δ 1.2 (bs, 2H), 2.9 (t, 2H), 3.12 (q, 2H), 4.7 (bs, 1H), 6.5 (d, 2H), 7.3 (d, 2H).

b) Ethyl 2-{2-(chloroacetyl)-2-(4-cyanoanilino)ethylamino}acetate (compound 1b)

Ethyl bromoacetate (84 g, 0.5 mol) is added to a suspension of 4-(2-aminoethylamino)benzonitrile (80.5 g, 0.5 mol) and diisopropylethylamine [DIEA] (65 g, 0.5 mol) in 800 ml of acetonitrile. Stirring is continued for 18 hours at room temperature. Most of the acetonitrile is evaporated off and the residue is taken up in dichloromethane. This solution is washed with water and dried over sodium sulphate; the crude product is passed through a short column of silica [eluent: dichloromethane and then (20/1 dichloromethane/methanol)] to give an oil.

The product obtained above is dissolved in 1 l of tetrahydrofuran. Diisopropylethylamine (51 g, 0.4 mol) is added, followed by slow addition of chloroacetyl chloride (45 g, 0.4 mol) at about 5° C. After stirring for 18 hours at room temperature, 1 l of ethyl acetate is added and the mixture is washed 3 times with water, dried over sodium sulphate and evaporated. A solid is obtained, which is stirred with a dichloromethane/ether (⅓) mixture. The suspension is filtered, rinsed with dichloromethane/ether (⅓) and dried under vacuum to give 100 g of a crystalline beige-coloured solid.

Yield:=62%; $^1$H-NMR (400 MHz, CDCl$_3$): δ 1.2 (q, 6H), 3.3 (m, 4H), 3.65 (m, 4H), 3.8 (s, 2H), 3.9 (d, 4H), 4.1 (s, 4H), 4.15 (q, 4H), 4.9 (t, 1H), 5.3 (t, 1H), 6.5 (dd, 4H), 7.3 (dd, 4H).

c) Ethyl 2-[4-(4-cyanophenyl)-2-oxopiperazino]acetate (compound 1c)

A suspension of ethyl 2-{2-(chloroacetyl)-2-(4-cyanoanilino)ethylamino}acetate (152 g, 0.47 mol), diisopropylethylamine (73 g, 0.57 mol) and sodium iodide (85 g, 0.57 mol) in 1200 ml of acetonitrile is refluxed for 2 hours. The solvent is evaporated off and the residue is taken up in dichloromethane and washed with water, dried over sodium sulphate and evaporated to give a brown oil, which is crystallized from a cyclohexane/ethyl acetate mixture to give 125 g of a brownish crystalline solid.

Yield=93%; Melting point=108° C.; $^1$H-NMR (400 MHz, CDCl$_3$): δ 1.3 (t, 3H), 3.65 (m, 4H), 4.05 (s, 2H), 4.2 (m, 4H), 6.8 (d, 2H), 7.5 (d, 2H).

d) 2-[4-(4-Cyanophenyl)-2-oxopiperazino]acetic acid (compound 1d)

Ethyl 2-[4-(4-cyanophenyl)-2-oxopiperazino]-acetate (20.7 g, 72 mmol) is dissolved in 80 ml of methanol, 80 ml of tetrahydrofuran and 100 ml of water, and lithium hydroxide monohydrate (4 g, 98 mmol) is then added with stirring. Stirring is continued for 20 minutes and the organic solvent is then removed under vacuum. About 100 ml of water are added to the suspension obtained and the mixture is acidified. The product is filtered off, rinsed with water and dried under vacuum at 50° C. to give 18.5 g of a beige-coloured powder.

Yield=100%; Melting point=215° C. (d). $^1$H-NMR (200 MHz, DMSO-d$_6$): δ 3.5 (t, 2H), 3.65 (t, 2H), 4.0 (s, 2H), 4.1 (s, 2H), 7.0 (d, 2H), 7.6 (d, 2H).

A-2: Synthesis of 2-[4-(4-cyanophenyl)-3-oxopiperazino] acetic acid (compound 2)

a) Ethyl 2-[2-(4-Cyanoanilino)ethyl(2-ethoxy-2-oxoethyl)amino]acetate (compound 2a)

A suspension of 4-(2-aminoethylamino)-benzonitrile (compound 1a) (32 g, 0.2 mol), potassium carbonate (55 g, 0.4 mol) and ethyl bromoacetate (67 g, 0.4 mol) in 400 ml of acetonitrile is refluxed for 18 hours. The crude product is filtered and passed through a short column of silica (eluent: dichloromethane) to give 58 g of a brown oil.

Yield=87%; $^1$H-NMR (200 MHz, CDCl$_3$):δ 6 1.3 (t, 3H), 3.05 (t, 2H), 3.4 (s, 2H), 3.55 (s, 2H), 3.8 (t, 2H), 4.2 (q, 2H), 7.45 (d, 2H), 7.6 (d, 2H). MS-Cl: m/z 287 (M+H)$^+$ b) 2-[4-(4-Cyanophenyl)-3-oxopiperazino]acetic acid (compound 2b)

A suspension of ethyl 2-[2-(4-cyanoanilino)ethyl(2-ethoxy-2-oxoethyl)amino]acetate (58 g, 0.174 mol), diisopropylethylamine (4 g, 0.03 mol) and potassium carbonate (24 g, 0.174 mol) in 400 ml of acetonitrile is refluxed for 2 days. The mixture is filtered and rinsed with dichloromethane. The filtrate is evaporated to give a brown solid, which is dissolved in 150 ml of methanol and 50 ml of water, followed by addition of lithium hydroxide monohydrate (8.4 g, 0.2 mol). After stirring for 30 minutes at room temperature, half of the methanol is removed under vacuum to give a suspension. About 100 ml of water are added and the mixture is acidified at 5° C. The product is filtered off, rinsed with water and dried under vacuum at 50° C. to give 27.2 g of a beige-coloured powder.

Yield=55%; Melting point=120° C. $^1$H-NMR (200 MHz, DMSO-d$_6$): δ 2.95 (t, 2H), 3.3 (s, 2H), 3.4 (s, 2H), 3.7 (t, 2H), 7.65 (d, 2H), 7.85 (d, 2H).

B—Preparation of the Intermediate Compounds of Formula IV

B-1: Synthesis of ethyl (2S)-3-{2-[(4-(4-cyanophenyl)-2-oxopiperazino)acetyl]amino}-2-[(phenylsulphonyl)-amino]propanoate (compound 3)

Isobutyl chloroformate (1.1 g, 8 mmol) is added, at about 5° C., to a suspension of 2-[4-(4-cyanophenyl)-2-oxopiperazino]acetic acid (1) (2.02 g, 7.8 mmol) and N-methylmorpholine (1.6 g, 15.8 mmol) in 50 ml of tetrahydrofuran. After 20 minutes at 5° C., ethyl (2S)-3-amino-2-(phenylsulphonylamino)propanoate hydrochloride (2.39 g, 7.8 mmol) is added. Stirring is continued for 18 hours to give a thick suspension. 100 ml of ethyl acetate are added and the product is filtered off, rinsed with water and then with ethyl acetate and ether, and dried to give 2.8 g of a white solid.

Yield=70%; $^1$H-NMR (400 MHz, DMSO-d$_6$): δ 1.0 (t, 3H), 3.2 (m, 1H), 3.4 (m, 3H), 3.45 (t, 2H), 3.8 (q, 2H), 3.95 (m, 5H), 7.0 (d, 2H), 7.55 (m, 5H), 7.75 (d, 2H), 8.15 (t, 1H), 8.4 (bd, 1H).

The method described above was used to synthesize the following compounds:

B-2: Ethyl (2S)-3-{2-[4-(4-cyanophenyl)-2-oxopiperazino)acetyl]amino}-2-[(3-pyridylsulphonyl)amino]propanoate (compound 4)

Starting material: ethyl (2S)-3-amino-2-[(3-pyridylsulphonyl)amino]propanoate dihydrochloride; Yield=74%; $^1$H-NMR (400 MHz, DMSO-d$_6$): δ 1.0 (t, 3H), 3.2 (m, 1H), 3.45 (m, 3H), 3.7 (t, 2H), 3.8 (q, 2H), 4.0 (m, 5H), 7.0 (d, 2H), 7.6 (m, 3H), 8.1 (dd, 1H), 8.15 (t, 1H), 8.70 (bs, 1H), 8.8 (d, 1H), 8.9 (d, 1H).

B-3: Ethyl (2S)-3-{2-[4-(4-cyanophenyl)-2-oxopiperazino)acetyl]amino}-2-[(8-quinolinylsulphonyl)amino]propanoate (compound 5)

Starting material: ethyl (2S)-3-amino-2-[(8-quinolinylsulphonyl)amino]propanoate dihydrochloride; Yield=70%; $^1$H-NMR (400 MHz, DMSO-d$_6$): δ 0.8 (t, 3H), 3.4 (m, 4H), 3.65 (m, 4H), 4.0 (m, 4H), 4.5 (bs, 1H), 7.0 (d, 2H), 7.6 (d, 2H), 7.75 (m, 2H), 7.85 (bs, 1H), 8.15 (t, 1H), 8.3 (dd, 2H), 8.6 (d, 1H), 9.05 (dd, 1H).

B-4: Ethyl (2S)-3-{2-[4-(4-cyanophenyl)-2-oxopiperazino)acetyl]amino}-2-[(benzylsulphonyl)amino]propanoate (compound 6)

Starting material: ethyl (2S)-3-amino-2-[(benzylsulphonyl)amino]propanoate hydrochloride; Yield=68%; $^1$H-NMR (400 MHz, DMSO-d$_6$): δ 1.2 (t, 3H), 3.4 (m, 4H), 3.65 (m, 2H), 3.95 (s, 2H), 4.05 (s, 2H), 4.08 (m, 1H), 4.1 (q, 2H), 4.35 (t, 2H), 6.95 (d, 2H), 7.35 (m, 5H), 7.6 (d, 2H), 7.7 (d, 1H), 8.1 (t, 1H).

B-5: Ethyl (2S)-3-{2-[4-(4-cyanophenyl)-2-oxopiperazino)acetyl]amino}-2-[(phenethylsulphonyl)amino]propanoate (compound 7)

Starting material: ethyl (2S)-3-amino-2-[(phenethylsulphonyl)amino]propanoate hydrochloride; Yield=63%; $^1$H-NMR (400 MHz, DMSO-d$_6$): δ 1.2 (t, 3H), 3.4 (m, 4H), 3.65 (m, 2H), 3.95 (s, 2H), 4.05 (s, 2H), 4.08 (m, 1H), 4.1 (q, 2H), 4.35 (t, 2H), 6.95 (d, 2H), 7.35 (m, 5H), 7.6 (d, 2H), 7.7 (d, 1H), 8.1 (t, 1H).

B-6: Ethyl (2S)-3-{2-[(4-(4-cyanophenyl)-2-oxopiperazino)acetyl]amino}-2-{[(4-methoxyphenyl)sulphonyl]amino}propanoate (compound 8)

Starting material: ethyl (2S)-3-amino-2-{[(4-methoxyphenyl)sulphonyl]amino}propanoate hydrochloride; Yield=70%; $^1$H-NMR (400 MHz, DMSO-d$_6$): δ 1.05 (t, 3H), 3.15 (m, 1H), 3.35 (m, 2H), 3.45 (m, 2H), 3.65 (m, 2H), 3.8–3.95 (m, 9H), 6.9 (d, 2H), 7.05 (d, 2H), 7.55 (d, 2H), 7.65 (d, 2H), 8.1 (t, 1H), 8.15 (bs, 1H).

B-7: Ethyl (2S)-3-{2-[(4-(4-cyanophenyl)-2-oxopiperazino)acetyl]amino}-2-{[(4-methylphenyl)sulphonyl]amino}propanoate (compound 9)

Starting material: ethyl (2S)-3-amino-2-[(4-toluenesulphonyl)amino]propanoate hydrochloride; Yield=55%; $^1$H-NMR (400 MHz, DMSO-d$_6$): δ 1.0 (t, 3H), 3.15 (m, 1H), 3.4 (m, 1H), 3.45 (m, 2H), 3.65 (m, 2H), 3.8 (q, 2H), 3.95 (m, 5H), 6.95 (d, 2H), 7.6 (d, 2H), 7.65 (d, 2H), 7.75 (d, 2H), 8.15 (t, 1H), 8.5 (bs, 1H).

B-8: Ethyl (2S)-3-{2-[(4-(4-cyanophenyl)-2-oxopiperazino)acetyl]amino}-2-{[(4-chlorophenyl)sulphonyl]amino}propanoate (compound 10)

Starting material: ethyl (2S)-3-amino-2-{[(4-chlorophenyl)sulphonyl]amino}propanoate hydrochloride; Yield=56%; $^1$H-NMR (400 MHz, DMSO-d$_6$): δ 1.0 (t, 3H), 3.15 (m, 1H), 3.4 (m, 1H), 3.45 (m, 2H), 3.65 (m, 2H), 3.8 (q, 2H), 3.95 (m, 5H), 6.95 (d, 2H), 7.6 (d, 2H), 7.65 (d, 2H), 7.75 (d, 2H), 8.15 (t, 1H), 8.5 (bs, 1H).

B-9: Ethyl (2S)-3-{2-[(4-(4-cyanophenyl)-2-oxopiperazino)acetyl]amino}-2-[(2-naphthylsulphonyl)amino]propanoate (compound 11)

Starting material: ethyl (2S)-3-amino-2-[(2-naphthylsulphonyl)amino]propanoate hydrochloride; Yield=54%; $^1$H-NMR (400 MHz, DMSO-d$_6$): δ 0.8 (t, 3H), 3.15 (m, 1H), 3.35 (m, 3H), 3.6 (m, 4H), 3.95 (m, 5H), 6.95 (d, 2H), 7.55 (d, 2H), 7.7 (m, 2H), 7.8 (d, 1H), 8.05 (d, 1H), 8.15 (m, 3H), 8.45 (s, 1H), 8.55 (d, 1H).

B-10: Ethyl (2S)-3-{2-[(4-(4-cyanophenyl)-2-oxopiperazino)acetyl]amino}-2-{[(benzyloxy)carbonyl]amino}propanoate (compound 12)

Starting material: ethyl (2S)-3-amino-2-{[(benzyloxy)carbonyl]amino}propanoate hydrochloride; Yield=49%; $^1$H-NMR (400 MHz, CDCl$_3$): δ 1.28 (t, 3H), 3.6 (m, 6H), 3.95 (s, 2H), 4.05 (s, 2H), 4.18 (m, 2H), 4.4 (m, 1H), 5.08 (s, 2H), 6.05 (bd, 1H), 6.75 (d, 2H), 7.06 (bs, 1H), 7.3 (m, 5H), 7.48 (d, 2H).

B-11: Ethyl (2S)-3-{2-[(4-(4-cyanophenyl)-2-oxopiperazino)acetyl]amino}-2-{(isobutoxycarbonyl)amino}propanoate (compound 13)

Starting material: ethyl (2S)-3-amino-2-{(isobutoxycarbonyl)amino}propanoate hydrochloride; Yield=51%; $^1$H-NMR (400 MHz, CDCl$_3$): δ 0.8 (d, 6H), 1.25 (t, 3H), 1.8 (m, 1H), 3.5–3.75 (m, 8H), 3.95 (s, 2H), 4.02 (s, 2H), 4.1 (m, 2H), 4.3 (m, 1H), 5.75 (d, 1H), 6.75 (d, 2H), 7.0 (bs, 1H), 7.45 (d, 2H).

B-12: Ethyl (2S)-3-{2-[(4-(4-cyanophenyl)-2-oxopiperazino)acetyl]amino}-2-{[butoxycarbonyl]amino}propanoate (compound 14)

Starting material: ethyl (2S)-3-amino-2-{(butoxycarbonyl)amino}propanoate hydrochloride; Yield=59%; $^1$H-NMR (400 MHz, CDCl$_3$): δ 0.9 (t, 3H), 1.25 (t, 3H), 1.35 (m, 2H), 1.55 (m, 2H), 3.6 (m, 6H), 4.0 (m, 6H), 4.2 (m, 2H), 4.4 (m, 1H), 5.75 (d, 1H), 6.75 (d, 2H), 7.05 (bt, 1H), 7.5 (d, 2H).

B-13: Ethyl (2S)-3-{2-[(4-(4-cyanophenyl)-2-oxopiperazino)acetyl]amino}-2-[(butylsulphonyl)amino]-propanoate (compound 15)

Starting material: ethyl (2S)-3-amino-2-[(butylsulphonyl)amino]propanoate trifluoroacetate; Yield=27%; $^1$H-NMR (400 MHz, CDCl$_3$): δ 0.9 (t, 3H), 1.25 (t, 3H), 1.4 (m, 2H), 1.7 (m, 2H), 2.95 (t, 2H), 3.4 (m, 1H), 3.6 (s, 4H), 3.7 (m, 1H), 3.95–4.2 (m, 7H), 5.9 (d, 1H), 6.95 (d, 2H), 7.1 (t, 1H), 7.45 (d, 2H).

B-14: Synthesis of methyl (2S)-3-{2-[(4-(4-cyanophenyl)-2-oxopiperazino)acetyl]amino}-2-{[1,1'-biphenyl)-4-ylsulphonyl]amino}propanoate (compound 16)

Bromotripyrrolidinophosphonium hexafluorophosphate [PyBroP®] (1.04 g, 2.23 mmol), DIEA (0.78 ml, 4.46 mmol) and methyl (2S)-3-amino-2-[(1,1'-biphenyl)-4-ylsulphonylamino]propanoate trifluoroacetate (0.5 g, 1.15 mmol) are added successively to a solution of 2-[4-(4-cyanophenyl)-2-oxopiperazino]acetic acid (compound 1) (0.29 g, 1.12 mmol) in 7 ml of DMF. Stirring is continued for 5 hours. Ethyl acetate is added and the organic phase is washed with 5% citric acid and then with water and dried over sodium sulphate. After chromatography on silica (9/1 dichloromethane/methanol), 0.58 g of a white solid is obtained.

Yield=90%; MS-ES: m/z 574 (M+H)+; $^1$H-NMR (270 MHz, CDCl$_3$): δ 3.15 (m, 1H), 3.50 (m, 4H), 3.55 (m, 4H), 4.05 (m, 5H), 6.45 (d, 1H), 6.75 (d, 2H), 7.55 (m, 8H), 7.65 (d, 2H), 7.85 (d, 2H).

The method described above was used to synthesize the following compounds:

B-15: Methyl (2S)-3-{2-[(4-(4-cyanophenyl)-2-oxopiperazino)acetyl]amino}-2-[3-trifluoromethylphenylsulphonyl)amino]propanoate (compound 17)

Starting material: methyl (2S)-3-amino-2-[(3-trifluoromethylphenylsulphonyl)amino]propanoate trifluoroacetate; Yield=83%; MS-ES: m/z 568 (M+H)+; $^1$H-NMR (270 MHz, CDCl$_3$): δ 3.50 (s, 5H), 3.65 (s, 4H), 4.05 (m, 4H), 4.20 (m, 1H), 6.65 (d, 1H), 6.75 (d, 2H), 7.25 (m, 1H), 7.50 (d, 2H), 7.60 (m, 1H), 7.80 (m, 1H), 8.00 (m, 1H), 8.10 (m, 1H).

B-16: Methyl (2S)-3-{2-[(4-(4-cyanophenyl)-2-oxopiperazino)acetyl]amino}-2-[(2-thiophenesulphonyl)amino]propanoate (compound 18)

Starting material: methyl (2S)-3-amino-2-[(2-thiophenesulphonyl)amino]propanoate trifluoroacetate; Yield=36%; $^1$H-NMR (270 MHz, CDCl$_3$): δ 3.50 (s, 5H), 3.65 (m, 2H), 3.75 (m, 2H), 4.00 (s, 3H), 4.05 (s, 2H), 7.00 (d, 2H), 7.20 (m, 1H), 7.55 (m, 3H), 7.90 (d, 1H). MS-ES: m/z 528 (M+Na)+.

B-17: Methyl (2S)-3-{2-[(4-(4-cyanophenyl)-2-oxopiperazino)acetyl]amino}-2-{[(3,5-dimethyl-4-isoxazolyl)sulphonyl]amino}propanoate (compound 19)

Starting material: methyl (2S)-3-amino-2-{[(3,5-dimethyl-4-isoxazolyl)sulphonyl]amino}propanoate trifluoroacetate; Yield=62%; MS-ES: m/z 517 (M−H)−.

B-18: Methyl (2S)-3-{2-[(4-(4-cyanophenyl)-2-oxopiperazino)acetyl]amino}-2-[(4-fluorophenylsulphonyl)amino]propanoate (compound 20)

Starting material: methyl (2S)-3-amino-2-[(4-fluorophenylsulphonyl)amino]propanoate trifluoroacetate; Yield=46%;

B-19: Methyl (2S)-3-{2-[(4-(4-cyanophenyl)-2-oxopiperazino)acetyl]amino}-2-[(1,3-benzodioxol-5-ylsulphonyl)amino]propanoate (compound 22)

Starting material: methyl (2S)-3-amino-2-[(1,3-benzodioxol-5-ylsulphonyl)amino]propanoate trifluoroacetate; Yield=37%; MS-ES: m/z 544 (M+H)+.

B-20: Methyl (2S)-3-{2-[(4-(4-cyanophenyl)-2-oxopiperazino)acetyl]amino}-2-[(isopropylsulphonyl)amino]propanoate (compound 23)

Starting material: methyl (2S)-3-amino-2-[(isopropylsulphonyl)amino]propanoate trifluoroacetate; Yield=30%; MS-ES: m/z 466 (M+H)+.

B-21: Synthesis of ethyl (2S)-3-{2-[(4-(4-cyanophenyl)-3-oxopiperazino)acetyl]amino}-2-[(phenylsulphonyl)amino]propanoate (compound 24)

Isobutyl chloroformate (1.47 g, 10.8 mmol) is added, at about 5° C., to a suspension of 2-[4-(4-cyanophenyl)-3-oxopiperazino]acetic acid (compound 2) (2.59 g, 10 mmol) and N-methylmorpholine (2.2 g, 21.8 mmol) in 50 ml of tetrahydrofuran, after which the mixture is stirred at room temperature for 20 minutes; ethyl 2-(S)-3-amino-2-(phenylsulphonylamino)propanoate hydrochloride (10.2 mmol) is then added. Stirring is continued for 18 hours. 100 ml of ethyl acetate and water are added and the organic phase is separated out by settling, washed with water and dried over sodium sulphate.

The crude product is purified by flash chromatography (15/1 dichloromethane/methanol) to give 2.5 g of a white solid.

Yield=48%; $^1$H-NMR (400 MHz, CDCl$_3$): δ 1.0 (t, 3H), 2.85 (m, 1H), 2.95 (m, 1H), 3.1 (s, 2H), 3.3 (m, 1H), 3.35 (s, 2H), 3.7 (m, 3H), 3.85 (q, 2H), 3.9 (bs, 1H), 5.7 (bs, 1H), 7.35 (m, 4H), 7.4 (m, 1H), 7.55 (d, 2H), 7.7 (d, 2H).

B-22: Synthesis of (2S)-3-{2-[(4-(4-cyanophenyl)-2-oxopiperazino)acetyl]amino}-2-[(phenylsulphonyl)amino]propanoic acid (compound 25)

Isobutyl chloroformate (2.9 g, 21.2 mmol) is added, at 5° C., to a suspension of 2-[4-(4-cyanophenyl)-2-oxopiperazino]acetic acid (compound 1) (5.18 g, 20 mmol) and N-methylmorpholine (2.5 g, 25 mmol) in 100 ml of tetrahydrofuran; after stirring for 20 minutes, a mixture of (2S)-3-amino-2-(phenylsulphonylamino)propanoic acid (5 g, 20.5 mmol) and diisopropylethylamine (2.8 g, 21.7 mmol) in 30 ml of water and 50 ml of THF is added. Stirring is continued for 2 hours. The organic solvent is evaporated off, water is added and the mixture is then acidified to give a suspension, which is extracted with ethyl acetate. The extracts are washed with water and dried over sodium sulphate. After flash chromatography (10/1/0.5 dichloromethane/methanol/AcOH), 4.6 g of product are obtained.

Yield=47%; $^1$H-NMR (400 MHz, DMSO-d$_6$): δ 3.2 (m, 1H), 3.35 (m, 1H), 3.45 (t, 2H), 3.65 (t, 2H), 3.95 (m, 4H), 7.0 (d, 2H), 7.2 (dt, 2H), 7.6 (m, 5H), 7.8 (d, 2H), 8.15 (t, 1H), 8.2 (d, 1H).

The following compound is synthesized according to the process described above:

B-23: (2S)-3-{2-[(4-(4-Cyanophenyl)-2-oxopiperazino)-acetyl]amino}-2-[(4-toluenesulphonyl)amino]propanoic acid (compound 26)

Starting material: (2S)-3-amino-2-[(4-toluenesulphonyl)amino]propanoic acid; Yield=55%; $^1$H-NMR (400 MHz, DMSO-d$_6$): δ 2.35 (s, 3H), 3.2 (m, 1H), 3.35 (m, 1H), 3.45 (t, 2H), 3.65 (t, 2H), 3.85–4.05 (m, 4H), 7.0 (d, 2H), 7.35 (d, 2H), 7.5 (d, 2H), 7.8 (d, 2H), 8.15 (t, 1H), 8.2 (d, 1H).

B-24: Synthesis of (2S)-3-{2-[(4-(4-cyanophenyl)-2-oxopiperazino)acetyl]amino}-2-{[(1,1'-biphenyl)-4-ylsulphonyl]amino}propanoic acid (compound 27)

A solution of methyl (2S)-3-{2-[(4-(4-cyanophenyl)-2-oxopiperazino)acetyl]amino}-2-{[(1,1'-biphenyl)-4-ylsulphonyl]amino}propanoate (compound 16) (0.6 g, 1.04 mmol) in 10 ml of THF and 1.2 ml of aqueous 1N LiOH solution is stirred at room temperature overnight. Ethyl acetate is added and the mixture is then acidified to pH 2 with 1N HCl. The organic phase is separated out after settling has taken place, the aqueous phase is extracted with ethyl acetate and the organic phases are combined, washed with water and dried over sodium sulphate; the solvent is evaporated off and the residue is chromatographed on silica [eluent: 10/1/0.5 dichloromethane/methanol/AcOH] to give 0.44 g of a white solid.

Yield=76%; MS-ES: m/z 562 (M+H)+; $^1$H-NMR (270 MHz, CDCl$_3$): δ 3.50 (m, 1H), 3.65 (m, 2H), 3.75 (m, 2H), 4.15 (s, 6H), 7.00 (d, 1H), 7.20 (m, 1H), 7.60 (m, 4H), 7.80 (m, 1H), 7.95 (d, 2H), 8.00 (d, 2H).

The method described above was used to synthesize the following compounds:

B-25: (2S)-3-{2-[(4-(4-Cyanophenyl)-2-oxopiperazino) acetyl]amino}-2-[3-trifluoromethylphenylsulphonyl)amino]propanoic acid (compound 28)

Starting material: compound 17; Yield=73%; MS-ES$^-$: m/z 552 (M−H)$^-$.

B-26: (2S)-3-{2-[(4-(4-Cyanophenyl)-2-oxopiperazino) acetyl]amino}-2-[(2-thiophenesulphonyl)amino]propanoic acid (compound 29)

Starting material: compound 18; Yield=88%; MS-ES$^-$: m/z 490 (M−H)$^-$; $^1$H-NMR (270 MHz, CDCl$_3$): δ 3.50 (m, 1H), 3.65 (m, 3H), 3.75 (m, 3H), 4.15 (s, 2H), 4.20 (s, 2H), 7.00 (d, 2H), 7.15 (m, 1H), 7.55 (d, 2H), 7.65 (m, 1H), 7.85 (m, 1H).

B-27: (2S)-3-{2-[(4-(4-Cyanophenyl)-2-oxopiperazino) acetyl]amino}-2-{[(3,5-dimethyl-4-isoxazolyl)sulphonyl]amino}propanoic acid (compound 30)

Starting material: compound 19; Yield=75%; MS-ES: m/z 504 (M)$^+$;

B-28: (2S)-3-{2-[(4-(4-Cyanophenyl)-2-oxopiperazino) acetyl]amino}-2-[(4-fluorophenylsulphonyl)amino]propanoic acid (compound 31)

Starting material: compound 20; Yield=59%; MS-ES$^-$: m/z 502 (M−H)$^-$.

B-29: (2S)-3-{2-[(4-(4-Cyanophenyl)-2-oxopiperazino) acetyl]amino}-2-[(1,3-benzodioxol-5-ylsulphonyl)amino]propanoic acid (compound 33)

Starting material: compound 22; Yield=82%; MS-ES: m/z 530 (M+H)$^+$;

B-30: (2S)-3-{2-[(4-(4-Cyanophenyl)-2-oxopiperazino) acetyl]amino}-2-[(isopropylsulphonyl)amino]propanoic acid (compound 34)

Starting material: compound 23; Yield=66%; $^1$H-NMR (400 MHz, DMSO-d$_6$): δ 1.24 (d, 6H), 3.20 (m, 1H), 3.25 (m, 2H), 3.50 (m, 2H), 3.70 (m, 2H), 4.00 (s, 4H), 6.40 (bs, 1H), 7.00 (d, 2 H), 7.60 (d, 2H), 8.05 (bs, 1H).

EXAMPLE 1

Synthesis of ethyl (2S)-3-{[2-(4-{4-[amino-(hydroxyimino)methyl]phenyl}-2-oxopiperazino) acetyl]amino}-2-[(phenylsulphonyl)amino] propanoate (CRL 42800)

A suspension containing ethyl (2S)-3-{2-[(4-(4-cyanophenyl)-2-oxopiperazino)acetyl]amino}-2-[(phenylsulphonyl)amino]propanoate (compound 3) (2.3 g, 4.48 mmol), triethylamine (1 g, 9.9 mmol) and hydroxylamine hydrochloride (0.68 g, 9.78 mmol) in 100 ml of ethanol is refluxed for 20 hours. The precipitate is filtered off, rinsed with ethanol and dried under vacuum to give 1.9 g of a white solid.

Yield=78%; MS-ES: m/z 569 (M+Na)$^+$. $^1$H-NMR (400 MHz, DMSO-d$_6$): δ 1.0 (t, 3H), 3.1 (m, 1H), 3.35 (m, 3H), 3.5 (bs, 2H), 3.75 (q, 2H), 3.8–4.0 (m, 5H), 5.65 (s, 2H), 6.85 (d, 2H), 7.55 (m, 5H), 7.75 (d, 2H), 8.1 (t, 1H), 8.35 (bd, 1H), 9.35 (bs, 1H).

The method described in Example 1 was used to synthesize the following compounds:

EXAMPLE 2

Ethyl (2S)-3-{[2-(4-{4-[amino(hydroxyimino) methyl]phenyl}-2-oxopiperazino)acetyl]amino}-2-[(3-pyridylsulphonyl)amino]propanoate (CRL 42814)

Starting material: compound 4; Yield=75%; MS-ES: m/z 570 (M+Na)$^+$; $^1$H-NMR (400 MHz, DMSO-d$_6$): δ 1.0 (t, 3H), 3.2 (m, 1H), 3.4 (m, 3H), 3.5 (m, 2H), 3.8 (q, 2H), 3.85 (s, 2H), 3.95 (q, 2H), 4.05 (dd, 1H), 5.65 (s, 2H), 6.9 (d, 2H), 7.55 (d, 2H), 7.6 (dd, 1H), 8.1 (dd, 2H), 8.7 (bs, 1H), 8.85 (d, 1H), 8.9 (d, 1H), 9.35 (bs, 1H).

EXAMPLE 3

Ethyl (2S)-3-{[2-(4-{4-[amino(hydroxyimino) methyl]phenyl}-2-oxopiperazino)acetyl]amino}-2-[(8-quinolinylsulphonyl)amino]propanoate (CRL 42813)

Starting material: compound 5; Yield=73%; $^1$H-NMR (400 MHz, DMSO-d$_6$): δ 0.85 (t, 3H), 3.35 (m, 4H), 3.55 (m, 4H), 3.85 (s, 2H), 3.95 (dd, 2H), 4.5 (dd, 1H), 5.7 (s, 2H), 6.9 (d, 2H), 7.55 (d, 2H), 7.75 (m, 2H), 7.9 (bd, 1H), 8.15 (t, 1H), 8.3 (m, 2H), 8.55 (d, 1H), 9.05 (d, 1H), 9.4 (s, 1H).

EXAMPLE 4

Ethyl (2S)-3-{[2-(4-{4-[amino(hydroxyimino) methyl]phenyl}-2-oxopiperazino)acetyl]amino}-2-[(benzylsulphonyl)amino]propanoate (CRL 42830)

Starting material: compound 6; Yield=64%; MS-ES: m/z 583 (M+Na)$^+$; $^1$H-NMR (400 MHz, DMSO-d$_6$): δ 1.2 (t, 3H), 3.3–3.55 (m, 7H), 3.85 (s, 2H), 4.0 (s, 2H), 4.1 (q, 2H), 4.4 (s, 2H), 5.65 (s, 2H), 6.9 (d, 2H), 7.35 (m, 5H), 7.55 (d, 2H), 7.75 (d, 1H), 8.05 (t, 1H), 9.4 (s, 1H).

EXAMPLE 5

Ethyl (2S)-3-{[2-(4-{4-[amino(hydroxyimino) methyl]phenyl}-2-oxopiperazino)acetyl]amino}-2-[(phenethylsulphonyl)amino]propanoate (CRL 42832)

Starting material: compound 7; Yield=82%; MS-ES: m/z 597 (M+Na)$^+$; $^1$H-NMR (400 MHz, DMSO-d$_6$): δ 1.25 (t, 3H), 3.0 (m, 2H), 3.25–3.6 (m, 9H), 3.85 (s, 2H), 4.05 (q, 2H), 4.2 (m, 2H), 5.7 (s, 2H), 6.9 (d, 2H), 7.3 (m, 5H), 7.6 (d, 2H), 7.9 (d, 1H), 8.15 (t, 1H), 9.4 (s, 1H).

EXAMPLE 6

Ethyl (2S)-3-{[2-(4-{4-[amino(hydroxyimino) methyl]phenyl}-2-oxopiperazino)acetyl]amino}-2-{[(4-methoxyphenyl)sulphonyl]amino}propanoate (CRL 42834)

Starting material: compound 8; Yield=87%; MS-ES: m/z 577 (M+H)$^+$; $^1$H-NMR (400 MHz, DMSO-d$_6$): δ 1.05 (t, 3H), 3.2 (m, 1H), 3.4 (m, 3H), 3.55 (m, 2H), 3.8–4.5 (m, 10H), 5.65 (s, 2H), 6.95 (d, 2H), 7.1 (d, 2H), 7.55 (d, 2H), 7.7 (d, 2H), 8.1 (t, 1H), 8.2 (d, 1H), 9.4 (s, 1H).

EXAMPLE 7

Ethyl (2S)-3-{[2-(4-{4-[amino(hydroxyimino) methyl]phenyl}-2-oxopiperazino)acetyl]amino}-2-{[4-toluenesulphonyl]amino)propanoate (CRL 42874)

Starting material: compound 9; Yield=83%; MS-ES: m/z 583 (M+Na)$^+$; $^1$H-NMR (400 MHz, DMSO-d$_6$): δ 1.0 (t, 3H), 2.35 (s, 3H), 3.1 (m, 1H), 3.3 (m, 4H), 3.4 (m, 2H), 3.7 (m, 3H), 3.9 (m, 3H), 5.6 (s, 2H), 6.85 (d, 2H), 7.4 (d, 2H), 7.5 (d, 2H), 7.6 (d, 2H), 8.05 (t, 1H), 8.25 (bd, 1H), 9.4 (s, 1H).

EXAMPLE 8

Ethyl (2S)-3-{[2-(4-{4-[amino(hydroxyimino) methyl]phenyl}-2-oxopiperazino)acetyl]amino}-2-{[(4-chlorophenyl)sulphonyl]amino}propanoate (CRL 42876)

Starting material: compound 10; Yield=67%; MS-ES: m/z 603 (M+Na)$^+$; $^1$H-NMR (400 MHz, DMSO-d$_6$): δ 1.05 (t, 3H), 3.2 (m, 1H), 3.35 (m, 4H), 3.5 (m, 2H), 3.9 (m, 6H), 5.7 (s, 2H), 6.9 (d, 2H), 7.6 (d, 2H), 7.7 (d, 2H), 7.75 (d, 2H), 8.15 (t, 1H), 8.55 (bs, 1H), 9.35 (bs, 1H).

EXAMPLE 9

Ethyl (2S)-3-{[2-(4-(4-[amino(hydroxyimino) methyl]phenyl}2-oxopiperazino)acetyl]amino}-2-[(2-naphthylsulphonyl)amino]propanoate (CRL 42878)

Starting material: compound 11; Yield=73%; MS-ES: m/z 619 (M+Na)$^+$; $^1$H-NMR (400 MHz, DMSO-d$_6$): δ 0.85 (t, 3H), 2.85 (m, 1H) 3.35 (m, 4H), 3.5 (t, 2H), 3.6 (m, 2H), 3.9 (m, 4H), 5.65 (s, 2H), 6.85 (d, 2H), 7.55 (d, 2H), 7.65 (m, 2H), 7.7 (d, 1H), 8.05 (d, 1H), 8.1 (dd, 3H), 8.35 (s, 1H), 8.5 (bd, 1H), 9.35 (s, 1H).

EXAMPLE 10

Ethyl (2S)-3-{[2-(4-{4-[amino(hydroxyimino) methyl]phenyl}-2-oxopiperazino)acetyl]amino}-2-{[(benzyloxy)carbonyl]amino}propanoate (CRL 42771)

Starting material: compound 12; Yield=49%; MS-ES: m/z 563 (M+Na)$^+$; $^1$H-NMR (400 MHz, DMSO-d$_6$): δ 1.1 (t, 3H), 3.35 (m, 6H), 3.78 (s, 2H), 3.9 (s, 2H), 4.0 (q, 2H), 4.1 (bq, 1H), 4.98 (s, 2H), 5.6 (s, 2H), 6.8 (d, 2H), 7.3 (m, 5H), 7.48 (d, 2H), 7.58 (d, 1H), 8.0 (bs, 1H), 9.3 (s, 1H).

EXAMPLE 11

Ethyl (2S)-3-{[2-(4-{4-[amino(hydroxyimino) methyl]phenyl}-2-oxopiperazino)acetyl]amino}-2-[(isobutoxycarbonyl)amino]propanoate (CRL 42893)

Starting material: compound 13; Yield=63%; MS-ES: m/z 529 (M+Na)$^+$; $^1$H-NMR (400 MHz, DMSO-d$_6$): δ 0.87 (d, 6H), 1.2 (t, 3H) 1.8 (m, 1H), 3.25–3.55 (m, 6H), 3.75 (q, 2H), 3.85 (s, 2H), 4.0 (s, 2H), 4.1 (q, 2H), 4.15 (m, 1H), 5.7 (s, 2H), 6.9 (d, 2H), 7.48 (d, 1H), 7.55 (d, 2H), 8.1 (t, 1H), 9.35 (s, 1H).

EXAMPLE 12

Ethyl (2S)-3-{[2-(4-{(4-[amino(hydroxyimino) methyl]phenyl}-2-oxopiperazino)acetyl]amino}-2-[(butoxycarbonyl)amino]propanoate (CRL 42895)

Starting material: compound 14; Yield=60%; MS-ES: m/z 529 (M+Na)$^+$; $^1$H-NMR (400 MHz, DMSO-d$_6$): δ 0.95 (t, 3H), 1.25 (t, 3H), 1.35 (m, 2H), 1.55 (m, 2H), 3.3–3.6 (m, 6H), 3.9 (s, 2H), 4.0 (t, 2H), 4.05 (s, 2H), 4.1 (q, 2H), 4.2 (m, 1H), 5.75 (s, 2H), 6.95 (d, 2H), 7.55 (d, 1H), 7.6 (d, 2H), 8.15 (t, 1H), 9.4 (s, 1H).

EXAMPLE 13

Ethyl (2S)-3-{[2-(4-{4-[amino(hydroxyimino) methyl]phenyl}-2-oxopiperazino)acetyl]amino}-2-[(butylsulphonyl)amino]propanoate (CRL 42905)

Starting material: compound 15; Yield=66%; MS-ES: m/z 549 (M+Na)$^+$; $^1$H-NMR (400 MHz, DMSO-d$_6$): δ 0.9 (t, 3H), 1.2 (t, 3H), 1.35 (m, 2H), 1.65 (m, 2H), 3.0 (m, 2H), 3.3 (m, 1H), 3.45 (m, 3H), 3.55 (m, 2H), 3.85 (s, 2H), 4.0 (s, 2H), 4.1 (m, 3H), 5.7 (s, 2H), 6.9 (d, 2H), 7.55 (d, 2H), 7.75 (d, 1H), 8.1 (t, 1H), 9.4 (s, 1H).

EXAMPLE 14

Ethyl (2S)-3-{[2-(4-{4-[amino(hydroxyimino) methyl]phenyl}-3-oxopiperazino)acetyl]amino}-2-[(phenylsulphonyl)amino]propanoate (CRL 42836)

Starting material: compound 24; Yield=73%; MS-ES: m/z 547 (M+H)$^+$; $^1$H-NMR (400 MHz, DMSO-d$_6$): δ 1.0 (t, 3H), 2.8 (t, 2H), 3.0 (dd, 2H), 3.2 (m, 2H), 3.4 (s, 2H), 3.45 (m, 1H), 3.7 (bt, 2H), 3.75 (q, 2H), 5.8 (s, 2H), 7.3 (d, 2H), 7.55 (m, 3H), 7.7 (d, 2H), 7.75 (d, 2H), 8.05 (t, 1H), 8.4 (bd, 1H), 9.65 (s, 1H).

EXAMPLE 15

Synthesis of (2S)-3-{[2-(4-{4-[amino (hydroxyimino)methyl]phenyl}-2-oxopiperazino) acetyl]amino}-2-[(phenylsulphonyl)amino] propanoic acid A suspension of (2S)-3-{2-[(4-(4-cyanophenyl)-2-oxopiperazino)acetyl]amino}-2-[(phenylsulphonyl)amino] propanoic acid (compound 25) (4.43 g, 9.13 mmol), triethylamine (2.3 g, 22.7 mmol) and hydroxylamine hydrochloride (1.58 g, 22.7 mmol) in 150 ml of ethanol is refluxed for 16 hours. The precipitate is filtered off, rinsed with ethanol and dried under vacuum to give 4.05 g of a beige-coloured solid.

Yield=86%; $^1$H-NMR (400 MHz, DMSO-d$_6$): δ 3.15 (m, 1H), 3.35–4.05 (m, 10H), 5.8 (s, 2H), 6.9 (d, 2H), 7.6 (m, 4H), 7.8 (d, 2H), 8.1 (m, 2H), 9.5 (bs, 1H).

The product described below is synthesized in the same way:

EXAMPLE 16

(2S)-3-{[2-4-{4-[amino(hydroxyimino)methyl] phenyl}-2-oxopiperazino)acetyl]amino}-2-{[4-toluenesulphonyl]-amino}propanoic acid Starting material: compound 26; Yield=55%; $^1$H-NMR (400 MHz, DMSO-d$_6$): δ 2.35 (s, 3H), 3.15 (m, 3H), 3.45–3.9 (m, 8H), 5.85 (s, 2H), 6.95 (d, 2H), 7.35 (d, 2H), 7.5 (d, 2H), 7.65 (d, 2H), 8.0 (bs, 1H), 8.05 (t, 1H), 9.5 (bs, 1H)

EXAMPLE 17

Synthesis of ethyl (2S)-3-{[2-(4-{4-[amino(imino) methyl]phenyl}-2-oxopiperazino)acetyl]amino}-2-[(phenylsulphonyl)amino]propanoate acetate (CRL 42817)

Ethyl (2S) -3-{[2- (4-{4-[amino(hydroxyimino)methyl] phenyl}-2-oxopiperazino)acetyl]amino}-2-[(phenylsulphonyl)amino]propanoate (Example 1) (1.5 g, 2.75 mmol) is dissolved in 50 ml of acetic acid. 600 mg of acetic anhydride (5.6 mmol) and 0.76 g of 10%; palladium-on-charcoal are added. The hydrogenolysis is carried out at room temperature under 50 psi for 3 hours. The catalyst is filtered off and the solution is evaporated to dryness. The solid obtained is dissolved in 150 ml of water and treated with charcoal. The solution is filtered. The filtrate is freeze-dried to give 1.3 g of a white solid.

Yield=80%; MS-ES: m/z 531 (M+H)$^+$; $^1$H-NMR (400 MHz, DMSO-d$_6$): δ 1.0 (t, 3H), 1.85 (bs, 3H), 3.2 (m, 1H), 3.35 (m, 1H), 3.45 (bs, 2H), 3.75 (bs, 2H), 3.85 (q, 2H), 3.95 (t, 3H), 4.05 (s, 2H), 7.05 (d, 2H), 7.6 (t, 2H), 7.65 (q, 1H), 7.8 (d, 4H), 8.3 (t, 5 1H).

The method described in Example 17 was used to synthesize the following compounds:

EXAMPLE 18

Ethyl (2S)-3-{[2-(4-{4-[amino(imino)methyl]phenyl}-2-oxopiperazino)acetyl]amino}-2-[(3-pyridylsulphonyl)amino]propanoate diacetate (CRL 42815)

Starting material: Example 2; Yield=74%; MS-ES: m/z 532 (M+H)$^+$; $^1$H-NMR (400 MHz, DMSO-d$_6$): δ 0.95 (t, 3H), 1.75 (bs, 6H), 3.2 (m, 1H), 3.4 (m, 1H), 3.45 (m, 3H), 3.62 (bs, 2H), 3.8 (q, 2H), 4.0 (m, 4H), 7.0 (d, 2H), 7.6 (dd, 1H), 2 0 7.7 (d, 2H), 8.1 (d, 1H), 8.25 (t, 1H), 8.8 (d, 1H), 8.9 (d, 1H).

EXAMPLE 19

Ethyl (2S)-3-{[2-(4-{4-[amino(imino)methyl]phenyl}-2-oxopiperazino)acetyl]amino}-2-[(1,2,3,4-tetrahydro-8-quinolinylsulphonyl)amino]propanoate acetate (CRL 42812)

Starting material: Example 3; Yield=77%; MS-ES: m/z 586 (M+H)$^+$; $^1$H-NMR (400 MHz, DMSO-d$_6$): δ 1.05 (t, 3H), 1.8 (m, 5H), 2.7 (t, 2H), 3.2 (m, 1H), 3.4 (m, 3H), 3.45 (bs, 2H), 3.65 (bs, 2H), 3.8 (m, 3H), 3.95 (m, 4H), 5.95 (s, 1H), 6.45 (t, 1H), 7.0 (m, 3H), 7.3 (d, 1H), 7.7 (d, 2H), 8.3 (t, 1H).

EXAMPLE 20

Ethyl (2S)-3-{[2-(4-{4-[amino(imino)methyl]phenyl}-2-oxopiperazino)acetyl]amino}-2-[(benzylsulphonyl)amino]propanoate acetate acetate (CRL 42829)

Starting material: Example 4; Yield 83%; MS-ES: m/z 545 (M+H)$^+$; $^1$H-NMR (400 MHz, DMSO-d$_6$): δ 1.2 (t, 3H), 1.8 (s, 3H), 3.35 (m, 2H), 3.45 (bs, 2H), 3.65 (bs, 2H), 4.1 (m, 7H), 4.4 (m, 2H), 7.05 (d, 2H), 7.35 (m, 5H), 7.75 (d, 2H), 8.3 (bs, 1H), 8.7 (bs, 1H), 10.9 (bs, 1H).

EXAMPLE 21

Ethyl (2S)-3-{[2-(4-{4-[amino(imino)methyl]phenyl}-2-oxopiperazino)acetyl]amino}-2-[(phenethylsulphonyl)amino]propanoate acetate (CRL 42831)

Starting material: Example 5; Yield=85%; MS-ES: m/z 559 (M+H)$^+$; $^1$H-NMR (400 MHz, DMSO-d$_6$): δ 1.2 (t, 3H), 1.85 (bs, 3H), 3.0 (m, 2H), 3.3 (m, 3H), 3.45 (m, 3H), 3.7 (bs, 2H), 4.05 (m, 7H), 7.05 (d, 2H), 7.25 (m, 1H), 7.3 (m, 4H), 7.8 (d, 2H), 8.45 (bs, 1H), 8.7 (bs, 1H), 10.9 (bs, 1H).

EXAMPLE 22

Ethyl (2S)-3-{[2-(4-{4-[amino(imino)methyl]phenyl}-2-oxopiperazino)acetyl]amino}-2-{[(4-methoxyphenyl)sulphonyl]amino}propanoate acetate (CRL 42833)

Starting material: Example 6; Yield=82%; MS-ES: m/z 561 (M+H)$^+$; $^1$H-NMR (400 MHz, DMSO-d$_6$): δ 1.0 (t, 3H), 1.75 (s, 3H), 3.2 (m, 1H), 3.35 (m, 1H), 3.4 (m, 3H), 3.7 (m, 2H), 3.8–4.0 (m, 9H), 7.05 (dd, 2H), 7.7 (dd, 4H), 8.3 (bs, 1H).

EXAMPLE 23

Ethyl (2S)-3-{[2-(4-{4-[amino(imino)methyl]phenyl}-2-oxopiperazino)acetyl]amino}-2-{[4-toluenesulphonyl]amino}propanoate acetate (CRL 42875)

Starting material: Example 7; Yield=63%; MS-ES: m/z 545 (M+H)$^+$; $^1$H-NMR (400 MHz, DMSO-d$_6$): δ 1.0 (t, 3H), 1.75 (bs, 3H), 2.4 (s, 3H), 3.2 (m, 1H), 3.35 (m, 1H), 3.4 (bs, 3H), 3.7 (bs, 2H), 3.85 (dd, 2H), 3.9 (q, 2H), 4.0 (s, 2H), 6.95 (d, 2H), 7.4 (d, 2H), 7.65 (d, 2H), 7.8 (d, 2H), 8.35 (bs, 1H).

EXAMPLE 24

Ethyl (2S)-3-{[2-(4-{4-[amino(imino)methyl]phenyl}-2-oxopiperazino)acetyl]amino}-2-{[(4-chlorophenyl)sulphonyl]amino}propanoate acetate (CRL 42877)

Starting material: Example 8; Yield=81%; MS-ES: m/z 565 (M+H)$^+$; $^1$H-NMR (400 MHz, DMSO-d$_6$): δ 1.0 (t, 3H), 1.8 (bs, 3H), 3.15 (m, 1H), 3.3 (m, 1H), 3.4 (bs, 2H), 3.65 (bs, 2H), 3.8 (m, 2H), 4.0 (m, 5H), 7.05 (d, 2H), 7.7 (d, 2H), 7.8 (dd, 2H), 8.3 (m, 1H), 8.8 (bs, 1H), 9.8 (bs, 1H).

EXAMPLE 25

Ethyl (2S)-3-{[2-(4-{4-[amino(imino)methyl]phenyl}-2-oxopiperazino)acetyl]amino}-2-[(2-naphthylsulphonyl)amino]propanoate acetate (CRL 42879)

Starting material: Example 9; Yield=82%; MS-ES: m/z 581 (M+H)$^+$; $^1$H-NMR (400 MHz, DMSO-d$_6$): δ 0.85 (t, 3H), 1.8 (bs, 3H), 3.2 (m, 1H), 3.35 (m, 3H), 3.65 (m, 4H), 3.9 (m, 5H), 7.0 (d, 2H), 7.7 (m, 5H), 8.0 (d, 1H), 8.15 (dd, 2H), 8.3 (t, 1H), 8.4 (bs, 1H), 8.7 (bs, 1H).

EXAMPLE 26

Ethyl (2S)-3-{[2-(4-{4-[amino(imino)methyl]phenyl}-2-oxopiperazino)acetyl]amino}-2-[(isobutoxycarbonyl)amino]propanoate acetate (CRL 42894)

Starting material: Example 11; Yield=76%; MS-ES: m/z 491 (M+H)$^+$; $^1$H-NMR (400 MHz, DMSO-d$_6$): δ 0.9 (d, 6H), 1.2 (t, 3H), 1.8 (bs, 3H), 1.95 (m, 1H), 3.25–3.5 (m, 5H), 3.7 (m, 4H), 3.9–4.15 (m, 6H), 7.0 (d, 2H), 7.55 (bs, 1H), 7.75 (d, 2H), 8.2 (bs, 1H).

EXAMPLE 27

Ethyl (2S)-3-{[2-(4-{4-[amino(imino)methyl]phenyl}-2-oxopiperazino)acetyl]amino}-2-[(butoxycarbonyl)amino]propanoate acetate (CRL 42896)

Starting material: Example 12; Yield=75%; MS-ES: m/z 491 (M+H)$^+$; $^1$H-NMR (400 MHz, DMSO-d$_6$): δ 0.85 (t, 3H), 1.2 (t, 3H), 1.35 (m, 2H), 1.5 (m, 2H), 1.75 (bs, 3H), 3.35 (m, 2H), 3.5 (bs, 4H), 3.7 (bs, 2H), 3.9 (t, 2H), 4.1 (m, 5H), 7.0 (d, 2H), 7.25 (bd, 1H), 7.75 (d, 2H), 8.2 (bs, 1H).

EXAMPLE 28

Ethyl (2S)-3-{[2-(4-{4-[amino(imino)methyl]phenyl}-2-oxopiperazino)acetyl]amino}-2-[(butylsulphonyl)amino]propanoate acetate (CRL 42906)

Starting material: Example 13; Yield=82%; MS-ES: m/z 511 (M+H)$^+$; $^1$H-NMR (400 MHz, DMSO-d$_6$): δ 0.9 (t, 3H), 1.2 (t, 3H), 1.35 (m, 2H), 1.65 (m, 2H), 1.75 (bs, 3H), 2.95 (m, 2H), 3.3 (m, 1H), 3.45 (m, 3H), 3.7 (bs, 2H), 4.1 (m, 6H), 7.05 (d, 2H), 7.75 (d, 2H), 8.3 (bs, 1H).

EXAMPLE 29

Ethyl (2S)-3-{[2-(4-{4-[amino(imino)methyl]phenyl}-3-oxopiperazino)acetyl]amino}-2-[(phenylsulphonyl)amino]propanoate acetate (CRL 42835)

Starting material: Example 14; Yield=93%; MS-ES: m/z 531 (M+H)$^+$; $^1$H-NMR (400 MHz, DMSO-d$_6$): δ 1.0 (t, 3H), 1.75 (bs, 3H), 2.75 (bs, 2H), 2.9 (dd, 2H), 3.2 (m, 1H), 3.35 (s, 2H), 3.45 (m, 1H), 3.7 (m, 4H), 3.9 (t, 1H), 7.55 (m, 5H), 7.75 (d, 2H), 7.85 (d, 2H), 8.2 (t, 1H), 9.2 (bs, 1H).

EXAMPLE 30

Synthesis of (2S)-3-{[2-(4-{4-[amino(imino)methyl] phenyl}-2-oxopiperazino)acetyl]amino}-2-[(phenylsulphonyl)amino]propanoic acid hydrochloride (CRL 42872)

(2S)-3-{[2-(4-{4-[Amino(hydroxyimino)methyl] phenyl}-2-oxopiperazino)acetyl]amino}-2-[(phenylsulphonyl)amino]propanoic acid (Example 15) (3.1 g, 6 mmol) is dissolved in 150 ml of acetic acid and 1.6 g of acetic anhydride (15.7 mmol) and 1.5 g of 10%; palladium-on-charcoal are added. The hydrogenolysis is carried out at room temperature under 50 psi for 4 hours. The mixture is filtered and evaporated to dryness, and 200 ml of water and 10 ml of 4N HCl are added. The mixture is treated with charcoal and then freeze-dried to give 1 g of a slightly yellow solid.

Yield=31%; MS-ES: m/z 503 (M+H)$^+$; $^1$H-NMR (400 MHz, DMSO-d$_6$): δ 3.2 (m, 1H), 3.4 (m, 1H), 3.45 (bs, 2H), 3.7 (bs, 2H), 3.95 (m, 5H), 7.05 (d, 2H), 7.65 (m, 3H), 7.85 (dd, 4H), 8.3 (m, 2H), 8.95 (bs, 2H), 9.2 (bs, 2H).

The following product is synthesized according to the process described above:

EXAMPLE 31

(2S)-3-{[2-(4-{4-[Amino(imino)methyl]phenyl}-2-oxopiperazino)acetyl]amino}-2-{[4-toluenesulphonyl]amino}propanoic acid hydrochloride (CRL 42873)

Starting material: Example 16; Yield=46%; MS-ES: m/z 517 (M+H)$^+$; $^1$H-NMR (400 MHz, DMSO-d$_6$): δ 2.2 (s, 3H), 3.05 (bs, 1H), 3.2 (m, 1H), 3.3 (m, 1H), 3.35 (bs, 2H), 3.7 (bs, 2H), 3.9 (m, 4H), 7.05 (d, 2H), 7.35 (d, 2H), 7.7 (d, 2H), 7.85 (d, 2H), 8.2 (d, 1H), 8.3 (bs, 1H), 9.0 (bs, 2H), 9.2 (bs, 2H).

EXAMPLE 32

Synthesis of (2S)-3-{[2-(4-{4-[amino(imino)methyl] phenyl}-2-oxopiperazino)acetyl]amino}-2-{[(1,1'-biphenyl)-4-ylsulphonyl]amino}propanoic acid trifluoroacetate (CRL 43203)

A suspension containing (2S)-3-{2-[(4-(4-cyanophenyl)-2-oxopiperazino)acetyl]amino}-2-{[(1,1'-biphenyl)-4-ylsulphonyl)amino}propanoic acid (compound 27) (0.65 g, 1.15 mmol), triethylamine (0.43 ml, 2.9 mmol) and hydroxylamine hydrochloride (0.2 g, 2.9 mmol) in 20 ml of ethanol is refluxed for 18 hours. The product is filtered off, rinsed with ethanol and dried under vacuum to give 0.42 g of a white solid.

The amidoxime obtained above (0.42 g, 0.71 mmol) is dissolved in 30 ml of acetic acid, and 0.175 ml of acetic anhydride (1.9 mmol) and 0.19 g of 10%; palladium-on-charcoal are added. The hydrogenolysis is carried out at room temperature under 50 psi for 4 hours. The catalyst is filtered off and evaporated to dryness to give a beige-coloured solid. Purification by HPLC (water/acetonitrile/0.2% TFA) followed by freeze-drying gives 8 mg of product.

MS-ES: m/z 579 (M+H)$^+$

The method described in Example 32 was used to synthesize the following compounds:

EXAMPLE 33

(2S)-3-{[2-(4-{4-[Amino(imino)methyl]phenyl}-2-oxopiperazino)acetyl]amino}-2-{[(4-fluorophenyl) sulphonyl]amino}propanoic acid trifluoroacetate (CRL 43204)

Starting material: compound 31; MS-ES: m/z 521 (M+H)$^+$; $^1$H-NMR (400 MHz, DMSO-d$_6$): δ 3.30 (m, 1H), 3.50 (m, 1H), 3.55 (bs, 2H), 3.80 (bs, 2H), 4.0–4.15 (m, 5H), 7.10 (d, 2H), 7.50 (t, 2H), 7.90 (m, 4H), 8.2 (bs, 1H), 8.4 (d, 1H), 9.0 (bs, 2H), 9.1 (bs, 2H).

EXAMPLE 34

(2S)-3-{[2-(4-{4-[Amino(imino)methyl]phenyl}-2-oxopiperazino)acetyl]amino}-2-{[(3-trifluoromethylphenylsulphonyl]amino}propanoic acid trifluoroacetate (CRL 43205)

Starting material: compound 28; MS-ES: m/z 571 (M+H)$^+$; $^1$H-NMR (400 MHz, DMSO-d$_6$): δ 3.20 (m, 1H), 3.45 (m, 3H), 3.70 (bs, 2H), 4.0–4.15 (m, 5H), 7.05 (d, 2H), 7.80 (d, 2H), 7.90 (d, 1H), 8.10 (bs, 3H), 8.15 (t, 1H), 8.50 (d, 1H), 8.65 (bs, 2H), 8.95 (bs, 2H).

EXAMPLE 35

(2S)-$^3$-{[2-(4-{4-[Amino(imino)methyl]phenyl}-2-oxopiperazino)acetyl]amino}-2-{[(3,5-dimethyl-4-isoxazolyl)sulphonyl]amino}propanoic acid trifluoroacetate (CRL 43206)

Starting material: compound 30; MS-ES: m/z 522 (M+H)$^+$; $^1$H-NMR (400 MHz, DMSO-d$_6$): δ 2.45 (s, 3H), 2.60 (s, 3H), 3.30 (m, 1H), 3.50 (m, 3H), 3.75 (bs, 2H), 4.0–4.15 (m, 5H), 7.10 (d, 2H), 7.95 (d, 2H), 7.90 (d, 1H), 8.30 (t, 1H), 8.60 (d, 1H), 8.90 (bs, 2H), 9.05 (bs, 2H).

EXAMPLE 36

(2S)-3-{[2-(4-{4-[Amino(imino)methyl]phenyl}-2-oxopiperazino)acetyl]amino}-2-[(2-thiophenesulphonyl)amino]propanoic acid trifluoroacetate (CRL 43207)

Starting material: compound 29; MS-ES: M/z 509 (M+H)$^+$;

EXAMPLE 37

(2S)-3-{[2-(4-{4-[Amino(imino)methyl]phenyl}-2-oxopiperazino)acetyl]amino}-2-[(1,3-benzodioxol-5-ylsulphonyl)amino]propanoic acid trifluoroacetate (CRL 43208)

Starting material: compound 33; MS-ES: m/z 547 (M+H)$^+$;

EXAMPLE 38

(2S)-3-{[2-(4-{4-[Amino(imino)methyl]phenyl}-2-oxopiperazino)acetyl]amino}-2-[(isopropylsulphonyl)amino]propanoic acid trifluoroacetate (CRL 43209)

Starting material: compound 34; MS-ES: m/z 469 (M+H)$^+$;

EXAMPLE 39

Ethyl (2S)-3-{[2-(4-{4-[amino[(ethoxycarbonyl) imino]methyl]phenyl}-2-oxopiperazino)acetyl] amino}-2-{[phenylsulphonyl]amino}propanoate (CRL 42959)

Ethyl (2S)-3-{[2-(4-{4-[amino(imino)methyl]phenyl}-2-oxopiperazino)acetyl]amino}-2-[(phenylsulphonyl)amino]

propanoate acetate (Example 17) is converted into the hydrochloride by addition of 2N hydrochloric acid solution followed by freeze-drying.

Triethylamine (1.25 g, 12.4 mmol) and ethyl chloroformate (0.65 g, 6 mmol) are successively added, at 5° C., to a solution of the hydrochloride thus obtained (2.83 g, 5 mmol) in 50 ml of DMF. Stirring is continued at room temperature for 18 hours. Water is added, the mixture is extracted with ethyl acetate and the extracts are dried over sodium sulphate. 1.2 g of a yellowish solid are obtained after chromatography on silica (10/1 ethyl acetate/methanol).

Yield=40%; MS-ES: m/z 625 (M+Na)$^+$; $^1$H-NMR (400 MHz, CDCl$_3$): δ 1.05 (t, 3H), 1.35 (t, 3H), 3.3 (m, 1H), 3.5–3.7 (m, 5H), 3.9 (q, 3H), 3.95–4.4 (m, 6H), 6.7 (d, 2H), 7.25 (t, 1H), 7.45 (t, 2H), 7.5 (m, 1H), 7.8 (d, 2H), 7.85 (s, 2H).

EXAMPLE 40

Ethyl (2S)-3-{[2-(4-{4-fimino(morpholino)methyl]phenyl}-2-oxopiperazino)acetyl]amino}-2-{[4-toluenesulphonyl]amino}propanoate (CRL 43100)

40 ml of a 4N hydrochloric ethyl acetate solution are added, at 5° C., to a mixture of ethyl (2S)-3-{2-[(4-(4-cyanophenyl)-2-oxopiperazino)acetyl]amino}-2-{[(4-methylphenyl)sulphonyl]amino}propanoate (compound 9) (2.45 g, 4.6 mmol) in 3 ml of ethanol. Stirring is continued at room temperature for 40 hours. The mixture is evaporated to dryness to give a beige-coloured solid.

Morpholine (1.6 g, 18 mmol) is added to a suspension of the imidate obtained above (1.4 g, 2.3 mmol) in 5 ml of ethanol and 40 ml of ethyl acetate. After stirring for 24 hours at room temperature, the crude product is filtered off and recrystallized from a mixture of ethyl acetate and ethanol to give 0.86 g of a white solid.

Yield=58%; MS-ES: m/z 615 (M+H)$^+$; $^1$H-NMR (400 MHz, DMSO-d$_6$): δ 1.05 (t, 3H), 2.4 (s, 3H), 3.2 (m, 1H), 3.3 (m, 1H), 3.45 (m, 2H), 3.6–3.7 (m, 10H), 3.8 (q, 2H), 3.9 (m, 2H), 4.0 (m, 3H), 7.1 (d, 2H), 7.35 (d, 2H), 7.5 (d, 2H), 7.65 (d, 2H), 8.35 (t, 1H), 8.4 (bs, 1H), 9.4 (bs, 2H).

The method described in Example 40 was used to synthesize the following compound:

EXAMPLE 41

Ethyl (2S)-3-{[2-(4-{4-[imino(piperidino)methyl]phenyl}-2-oxopiperazino)acetyl]amino}-2-{[4-toluenesulphonyl]amino}propanoate (CRL 43117)

Starting materials: compound 9 and piperidine; Yield= 27%; MS-ES: m/z 613 (M+H)$^+$; $^1$H-NMR (400 MHz, DMSO-d$_6$): δ 1.05 (t, 3H), 1.55 (m, 2H), 1.65 (m, 4H), 2.35 (s, 3H), 3.2 (m, 1H), 3.3 (m, 1H), 3.4 (m, 4H), 3.65 (m, 4H), 3.8 (q, 2H), 3.9 (m, 2H), 4.0 (m, 2H), 7.05 (d, 2H), 7.35 (d, 2H), 7.45 (d, 2H), 7.65 (d, 2H), 8.25 (t, 1H), 8.35 (bs, 1H), 9.05 (bs, 1H), 9.15 (bs, 1H).

A study of the inhibitory activity of the compounds of formula (I) on platelet aggregation was carried out in vitro, i.e. by direct contact of solutions of variable concentrations of the compounds with platelets freshly separated from a sample of total blood, taken under standardized conditions, from laboratory animals (guinea pigs) and from healthy human subjects who have not received any substances or drugs that might interfere with blood clotting. The anti-platelet-aggregating activity was also studied ex vivo/vitro, i.e. after administration of the substances claimed to guinea pigs to measure the intensity and duration of the anti-aggregating action induced by the fraction of the test product absorbed and circulating in the blood.

1. In vitro Pharmacological Studies
1.1. Studies on Guinea Pig Platelets

Blood is taken by intracardiac puncture from male Dunkin-Hartley guinea pigs (weighing about 330 g), at a rate of 4.5 ml per 0.5 ml of trisodium citrate (concentration of the aqueous solution: 1.55%;) in order to prevent all trace of clotting. The platelet-rich plasma (PRP) is obtained by centrifuging the tubes of total blood for 15 minutes at 150 g.

The PRPs are collected as "pools". The platelets contained in these pools are counted using a Coulter ZM haematology automatic device: if necessary, a dilution is carried out in order for the platelet concentration in the plasma to be between 200000 and 400000 platelets/mm$^3$. Simultaneously, other samples of these pools serve to prepare the platelet-poor plasma (PPP) by centrifugation at 1500 g for 15 minutes.

The kinetic study of the platelet aggregation is carried out by adding a collagen solution (1 μg/ml) to a volume of PRP, using a Chrono-log Corporation aggregometer (490-D$_1$, or 560 VS) which uses an optical detection of the appearance of the thrombus.

The determination of the 50%; inhibitory concentration (IC$_{50}$) is carried out by adding a given volume of solvent (control reference) and increasing concentrations: $1.5 \times 10^{-8}$ M, $7 \times 10^{-8}$ M, $1.5 \times 10^{-7}$ M, $3 \times 10^{-7}$ M, $7 \times 10^{-7}$ M, $1.5 \times 10^{-6}$ M and $7 \times 10^{-5}$ M, of the compounds to samples of the pools of PRP. The measurements of the aggregation inhibition are carried out after 3 minutes of contact at 37° C. with agitation.

1.2 Study on Human Platelets

Venous blood is taken from a group of ten healthy human subjects of the same age, by puncture into a vein of the fold of the elbow and is collected in a glass tube containing aqueous 0.129 M sodium citrate solution (1 volume of citrate solution per 9 volumes of blood). Each tube is then centrifuged a first time at 20° C. and 100 g for 15 minutes in order to obtain the platelet-rich plasma (PRP); after removing this PRP, the tube is again centrifuged at 2000 g for 15 minutes in order this time to remove the platelet-poor plasma (PPP).

For each identified sample of PRP, the platelets are counted using a Coulter ZM counter. Each sample is then used to study the variation in inhibition of the platelet aggregation triggered by the addition of a Chromo-par-Reagent collagen glucose solution from Coultronics (used at a concentration of 5 μg/ml) as a function of the addition of increasing concentrations of each compound in a range covering the interval $10^{-8}$ M→$10^{-5}$ M, (example of concentrations: $10^{-8}$ M, $5 \times 10^{-7}$ M, $3 \times 10^{-7}$ M, $10^{-7}$ M, $8 \times 10^{-6}$ M, $6 \times 10^{-6}$ M, $4 \times 10^{-6}$ M, $2 \times 10^{-6}$ M, $10^{-6}$ M, $5 \times 10^{-5}$ M, $10^{-5}$ M). Beforehand, for each compound, an aqueous $10^{-3}$ M solution is prepared. A control test intended to check the possible effect of the solvents (reference value) on the platelet aggregation is introduced into each measurement series, and the aggregation is measured after 3 minutes of contact at 37° C. with agitation.

From the percentages of inhibition of the platelet aggregation measured for each concentration of each compound, the 50%; inhibitory concentration (IC$_{50}$) is calculated.

2. Ex vivo/vitro Pharmacological Study in Guinea Pigs

Evaluation of the anti-platelet-aggregating activity of the compounds is carried out in the same guinea pigs as those mentioned above (Dunkin-Hartley strain). The administration of each product in a range of doses from 150 mg/kg to 10 mg/kg and of each vehicle (5 ml/kg) is carried out via the gastric route (g.r.) 1 h, 2 h, 4 h, 6 h, 8 h or 12 h before blood is taken from the guinea pigs fasted the day before. The allocation of the treatments to the animals is random.

The blood is taken and then treated under the same conditions as those described above for the in vitro studies.

The results of the inhibition of the platelet aggregation obtained for each test concentration make it possible to calculate the $IC_{50}$ concentration of each test product and the kinetics of the inhibitory effect and their duration of action.

The results are collated in the following table:

| | | | | % of g.r. inhibition guinea pig ex vivo | | | |
| | Com- | $IC_{50}$(M) in vitro | | d = 150 mg/kg | | d = 10 mg/kg | |
| Examples | pound CRL | Guinea pig | Man | 1 h | 2 h | 1 h | 2 h |
| --- | --- | --- | --- | --- | --- | --- | --- |
| 1 | 42800 | — | — | −79 | −76 | — | — |
| 17 | 42817 | $1.1 \times 10^{-7}$ | $1.0 \times 10^{-5}$ | −71 | −59 | −37 | −39 |
| 18 | 42815 | $9.1 \times 10^{-7}$ | $3.2 \times 10^{-5}$ | −51 | — | — | — |
| 19 | 42812 | $2.5 \times 10^{-7}$ | $8.2 \times 10^{-6}$ | −59 | — | −19 | — |
| 24 | 42877 | $3.2 \times 10^{-7}$ | $9.3 \times 10^{-6}$ | — | — | −21 | — |
| 29 | 42835 | $1.8 \times 10^{-6}$ | $5.3 \times 10^{-6}$ | −59 | −46 | — | — |
| 30 | 42872 | $9.4 \times 10^{-8}$ | $1.2 \times 10^{-7}$ | — | — | −68 | −64 |
| 31 | 42873 | $3.1 \times 10^{-7}$ | $3.4 \times 10^{-7}$ | — | — | −49 | — |
| 23 | 42875 | $4.2 \times 10^{-7}$ | $1.8 \times 10^{-5}$ | — | — | −4 | — |
| 25 | 42879 | $2.0 \times 10^{-7}$ | $9.5 \times 10^{-5}$ | −59 | −46 | −6 | — |
| 26 | 42894 | $4.0 \times 10^{-7}$ | $5.7 \times 10^{-6}$ | — | — | −12 | — |
| 40 | 43100 | $1.0 \times 10^{-6}$ | — | — | — | −60 | −35 |
| 41 | 43117 | $1.6 \times 10^{-6}$ | — | — | — | −12 | — |
| 39 | 42959 | — | — | — | — | −58 | — |

— data not available.

A subject of the present invention is thus also pharmaeutical compositions comprising an effective amount of a compound of formula (I) or one of the salts thereof with pharmaceutically acceptable acids.

A subject of the invention is, more particularly, compounds for inhibiting the aggregation of blood platelets, comprising an effective amount of one of these compounds.

A subject of the invention is also
- a process for inhibiting the binding of fibrinogen to the blood platelets in a mammal, comprising the administration to this mammal of an effective amount of one of these compounds,
- a process for treating a thrombosis in a patient, comprising the administration to this patient of an effective amount of one of these compounds,
- a process for preventing the risk of thrombosis in a patient, comprising the administration to this patient of an effective amount of one of these compounds.

The compounds of formula (I) can be used, most particularly by, in the following fields:

i) acute prevention of the arterial thrombotic risk in the course of heart surgery (coronary bypass) or interventional cardiology (transluminal percutaneous angioplasty, endartectomy, insertion of a stent):

in these situations, the compounds are added to the recognized preventive treatment of the arterial thrombotic risk; oral administration of acetylsalicylic acid starting before the intervention (150 to 500 mg/day orally) and then continues as follows; intravenous infusion of non-fractionated heparin starting during the intervention and then continuing for 48 to 96 hours. The administration of the compound of formula I can then be carried out either orally (0.5 to 1.5 mg/kg) at the same time as the administration of aspirin, or by intravenous infusion (0.25 to 1 mg/kg/24 h) combined or not combined with a bolus. After the 48th hour, if the treatment was administered intravenously, it will be relayed by the oral administration (0.25 to 10 mg/kg in two dosage intakes with an interval of 12 hours) in order to facilitate the hospitalization care and then the ambulatory treatment care.

(ii) Secondary prophylaxis of the arterial thrombotic risk in patients liable to exhibit episodes of unstable angina or a myocardial infarction: in these situations, the large bioavailability of the compounds claimed, i.e. the possibility of rapidly obtaining circulating concentrations that are effective since they are capable of inhibiting the binding of fibrinogen to platelets, makes it possible to use the medicinal products claimed orally during the period in which the patients show this risk of arterial thrombosis. In these situations, these compounds may be administered advantageously at a rate of 1 to 3 oral intakes per day, by virtue of their high bioavailability and their long duration of action, the dose being chosen in the range 0.5–10 mg/kg.

The pharmaceutical compositions which comprise one of the active principles described in the present patent application incorporate the active substance either in the form of a base or in the form of a pharmaceutically acceptable salt, or alternatively in the form of a prodrug comprising an ester function, this function then being released in vivo after oral administration. These pharmaceutical compositions incorporate the manufacturing adjuvants and vehicles that are known to those skilled in the art. The latter are chosen from the range of pharmaceutical tools recognized by the Pharmacopoeias. Examples which may be mentioned for the preparation of pharmaceutical forms intended for the oral route are: starch, magnesium stearate, talc, gelatin, agar, pectin, lactose, polyethylene glycols, etc. The pharmaceutical forms which can be used will be chosen from the following possibilities: splittable or non-splittable tablets, capsules, lozenges, granules, powders. According to the characteristics of the pathology to be treated and the morphology of each patient, the daily oral dose will be between 0.02 and 50 mg/kg/day taken in 1 to 3 doses uniformly spaced in order to maintain an effective level of occupation of the platelet GpIIb/IIIa receptors. Via the intravenous route, the pharmaceutical forms intended for the acute phase of the treatment are designed so as to allow an individual dosage adaptation on the basis of the inhibition of platelet aggregation which is most efficient as a function of the immediate evolution of the operation follow-up. In this context, the lyophilizate and the ready-to-use solution for infusion make it possible to individually modify the dosage within the dosage range 0.01 mg/kg/day–20 mg/kg/day.

What is claimed is:

1. Compounds of general formula (I):

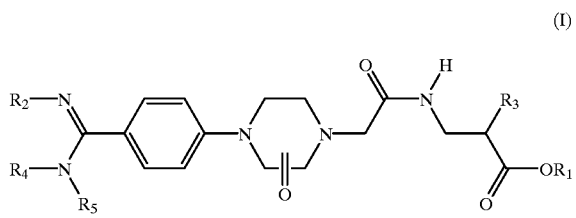

(I)

in which:

$R_1$ is chosen from hydrogen, a $C_1$–$C_4$ alkyl group and a phenyl ($C_1$–$C_4$ alkyl) group;

$R_2$ is chosen from hydrogen, a hydroxyl group and a protecting group for the amidino group selected from the group consisting of ethoxycarbonyl, benzyloxycarbonyl, p-nitrobenzyloxycarbonyl and tert-butoxycarbonyl;

$R_3$ is chosen from the groups of formula:

—NH—CO—$R_6$, and NHSO$_2$$R_7$ $R_6$ being chosen from $C_1$–$C_4$ alkoxy, $C_3$–$C_7$ cycloalkoxy, benzyloxy, methoxyphenyl, dimethoxyphenyl, benzodioxolyl and benzodioxanyl groups and in the group of formula:

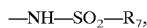
—NH—SO$_2$—R$_7$, $R_7$ being chosen from:
  $C_1$–$C_5$ alkyl groups optionally substituted with one or more groups chosen from halogens, hydroxyl groups and the trifluoromethyl group;
  mono- or bicyclic $C_3$–$C_{12}$ cycloalkyl groups;
  mono-, bi- or tricyclic $C_6$–$C_{14}$ aryl groups;
  heteroaryl groups chosen from pyridyl, thienyl, quinolyl, benzodioxanyl, benzodioxolyl and isoxazolyl groups;
  phenyl ($C_1$–$C_4$) alkyl and naphthyl ($C_1$–$C_4$) alkyl group;

or $R_7$ is the groups of formula:

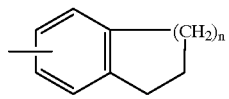

in which n=1, 2 or 3;
  the aryl or heteroaryl groups of $R_7$ optionally being substituted with one or more groups chosen independently from halogens, $C_1$–$C_4$ alkyl, trifluoromethyl, $C_1$–$C_4$ alkylthio, $C_1$–$C_4$ alkyloxy, $C_1$–$C_4$ alkylsulphonyl, nitro, di (($C_1$–$C_4$)alkyl) amino, phenyl, naphthyl and heteroaryl groups chosen from thienyl, furyl and pyridyl groups, and from groups —COOR, —CH$_2$—COOR or —O—CH$_2$COOR, R being a $C_1$–$C_4$ alkyl group,
  $R_4$ and $R_5$ are chosen, independently of each other, from hydrogen, a $C_1$–$C_5$ alkyl group or form, together with the nitrogen atom, a group chosen from piperidyl and morpholinyl groups,
  and the oxo group is in position 2 or 3 on the piperazine; and the addition salts thereof with pharmaceutically acceptable acids.

2. Compounds according to claim 1, in which $R_3$ is a group —NH—SO$_2$—R$_7$.

3. Compounds according to claim 2, in which $R_7$ is chosen from phenyl and tolyl groups.

4. Compounds according to claim 3, which are chosen from
  ethyl (2S)-3-{[2-(4-{4-[amino(imino)methyl]phenyl}-2-oxopiperazino)acetyl]amino}-2-[(phenylsulphonyl)amino]propanoate;
  (2S)-3-{[2-(4-{4-[amino(imino)methyl]-phenyl}-2-oxopiperazino)acetyl]amino}-2-[(phenylsulphonyl)amino]propanoic acid,
  (2S)-3-{[2-(4-{4-[amino[(ethoxycarbonyl)imino]methyl]phenyl}-2-oxopiperazino)acetyl]amino}-2-{[phenylsulphonyl]amino}propanoic acid,
  ethyl (2S)-3-{[2-(4-{4-[imino(morpholino)methyl]phenyl}-2-oxopiperazino)acetyl]amino}-2-{[4-toluenesulphonyl]amino}propanoate,
  (2S)-3-{[2-(4-{4-[amino(imino)methyl]phenyl}-2-oxopiperazino)acetyl]amino}-2-{[4-toluenesulphonyl]amino}propanoic acid,
and the addition salts thereof with pharmaceutically acceptable acids.

5. Process for preparing compounds of formula (I) according to claim 1, by:

a) reacting an acid of formula

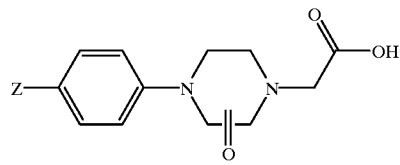
(II)

in which Z is a precursor group of a group

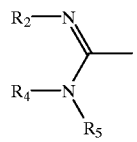

with an amine of formula

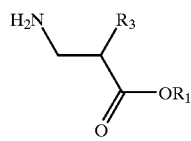
(III)

to give a compound of formula

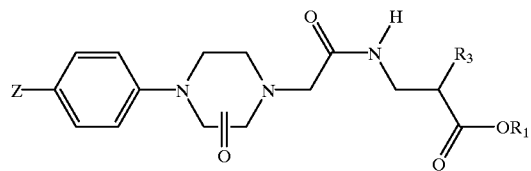
(IV)

and b) converting the group Z into a group

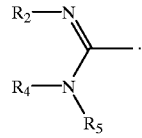

6. Antithrombotic composition which comprises an effective amount of a compound according to claim 1 in association with a pharmaceutically acceptable vehicle.

7. Process for avoiding the formation of a thrombus in a patient, by inhibiting the aggregation of blood platelets comprising the administration to this patient of an effective amount of a compound according to claim 1.

8. Process for treating a thrombosis in a patient, comprising the administration to this patient of an effective amount of a compound according to claim 1.

* * * * *